(12) United States Patent
Chang et al.

(10) Patent No.: US 8,703,411 B2
(45) Date of Patent: Apr. 22, 2014

(54) CRYOPRESERVATION OF UMBILICAL CORD TISSUE FOR CORD TISSUE-DERIVED STEM CELLS

(75) Inventors: Hsiu-Kang Chang, Taipei (TW); Wei-Yu Lo, Taipei (TW)

(73) Assignee: HealthBanks Biotech Co., Ltd., Taipei (TW)

( * ) Notice: Subject to any disclaimer, the term of this patent is extended or adjusted under 35 U.S.C. 154(b) by 77 days.

(21) Appl. No.: 13/245,145

(22) Filed: Sep. 26, 2011

(65) Prior Publication Data
US 2013/0059286 A1 Mar. 7, 2013

(30) Foreign Application Priority Data
Sep. 1, 2011 (TW) .............................. 100131519 A

(51) Int. Cl.
*A01N 1/02* (2006.01)
*C12N 5/073* (2010.01)

(52) U.S. Cl.
CPC ................................... *C12N 5/0605* (2013.01)
USPC ......................................................... 435/1.3

(58) Field of Classification Search
USPC .......................................................... 435/1.3
See application file for complete search history.

(56) References Cited

U.S. PATENT DOCUMENTS

| 2009/0142830 A1 | 6/2009 | Yamashiro | |
| 2009/0170059 A1* | 7/2009 | Klingemann | 435/1.3 |
| 2009/0275127 A1* | 11/2009 | Ennis et al. | 435/366 |
| 2010/0216237 A1* | 8/2010 | Ganchas Soares et al. | 435/366 |

FOREIGN PATENT DOCUMENTS

| CN | 101922048 A | 12/2010 |
| CN | 101974484 B | 1/2013 |

OTHER PUBLICATIONS

Meyer TPH, Hofmann B, Zaisserer J, Jacobs VR, Fuchs B, Rapp S, Weinauer F, Burkhart J. "Analysis and cryopreservation of hematopoietic stem and progenitor cells from umbilical cord blood", Cytotherapy 2006, vol. 8, 265-276.*
Freshney, R.I. Culture of Animal Cells: A Manual of Basic Technique, 4th Ed.; Wiley-Liss: New York, 2000; pp. 159-173.*

* cited by examiner

*Primary Examiner* — Allison Ford
*Assistant Examiner* — Michelle F Paguio Frising
(74) *Attorney, Agent, or Firm* — Hsiu-Ming Saunders; Intellectual Property Connections, Inc.

(57) ABSTRACT

A method of preserving an umbilical cord is disclosed. The method comprises obtaining a segment of an umbilical cord; mincing the segment of the umbilical cord into cord tissue pieces; admixing the cord tissue pieces with a cryogenic composition comprising a cryoprotectant and a protein to form a mixture; shaking the mixture for a duration of no shorter than 20 minutes and no longer than 40 minutes; and cryopreserving the mixture.

16 Claims, 9 Drawing Sheets

Cobble stone

CRYOPRESERVATION OF UMBILICAL CORD TISSUE FOR CORD TISSUE-DERIVED STEM CELLS

REFERENCES TO RELATED APPLICATION

This application claims priority to the Taiwan Application Serial Number 100131519, filed Sep. 1, 2011, herein incorporated by reference in its entirety.

FIELD OF THE INVENTION

The present invention relates generally to stem cells, and more specifically to umbilical cord tissue-derived stem cells.

BACKGROUND OF THE INVENTION

The potential benefits of preserving a baby's umbilical cord blood have been proposed. Now scientists are taking it one step further to preserve the actual umbilical cord tissue. The ideas is that a section of umbilical cord at birth and all of the cells within it may be stored. The cord tissue is frozen in a cryogenic storage tanks for long-term preservation. If the baby's cells are needed for therapies in the future, the cord tissue can be processed to extract the cells using the best technology at that time.

The Wharton's Jelly of the umbilical cord (cord tissue) is a rich source of pluripotent mesenchymal stem cells (MSC), which have great potential in regenerative medicine. MSC can differentiate into bone, cartilage, nerve, adipose, cardiac, smooth muscle, hepatic and skin cells.

Since this is a rather new area of preservation and subsequent cell culturing, there is a need for efficient protocols.

SUMMARY OF THE INVENTION

In one aspect, the invention relates to a method of preserving an umbilical cord. The method comprises: obtaining an umbilical cord; mincing the umbilical cord into cord tissue pieces, wherein each of the cord tissue pieces has a size of no larger than 2 mm; admixing the cord tissue pieces with a cryogenic composition comprising a cryoprotectant and a protein to form a mixture; shaking the mixture for a duration of no shorter than 28 minutes and no longer than 32 minutes; and cryopreserving the mixture.

In another aspect, the invention relates to a method of A method of preserving an umbilical cord, comprising: obtaining an umbilical cord; mincing the umbilical cord into cord tissue pieces; admixing the cord tissue pieces with a cryogenic composition comprising a cryoprotectant and a protein to form a mixture; shaking the mixture for a duration of no shorter than 20 minutes and no longer than 40 minutes; and cryopreserving the mixture.

Further in another aspect, the invention relates to a method of obtaining umbilical cord tissue-derived stem cells from an umbilical cord, comprising: obtaining an umbilical cord; mincing the umbilical cord into cord tissue pieces; admixing the cord tissue pieces with a cryogenic composition comprising a cryoprotectant and a protein to form a mixture; shaking the mixture for a duration of no shorter than 20 minutes and no longer than 40 minutes; and cryopreserving the mixture; thawing the mixture and removing the cryogenic composition; and culturing the cord tissue pieces in a culture media to obtain the umbilical cord-derived stem cells.

Further in another aspect, the invention relates to a cryogenic composition comprising: a) albumin or human serum; and b) a cryoprotectant, wherein the composition is free of non-human animal-derived components.

Yet in another aspect, the invention relates to a cryogenic composition comprising human cord blood serum 30~50% or albumin 2.5~25%; DMSO 5.5~55%; and dextran 0.5~5%.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
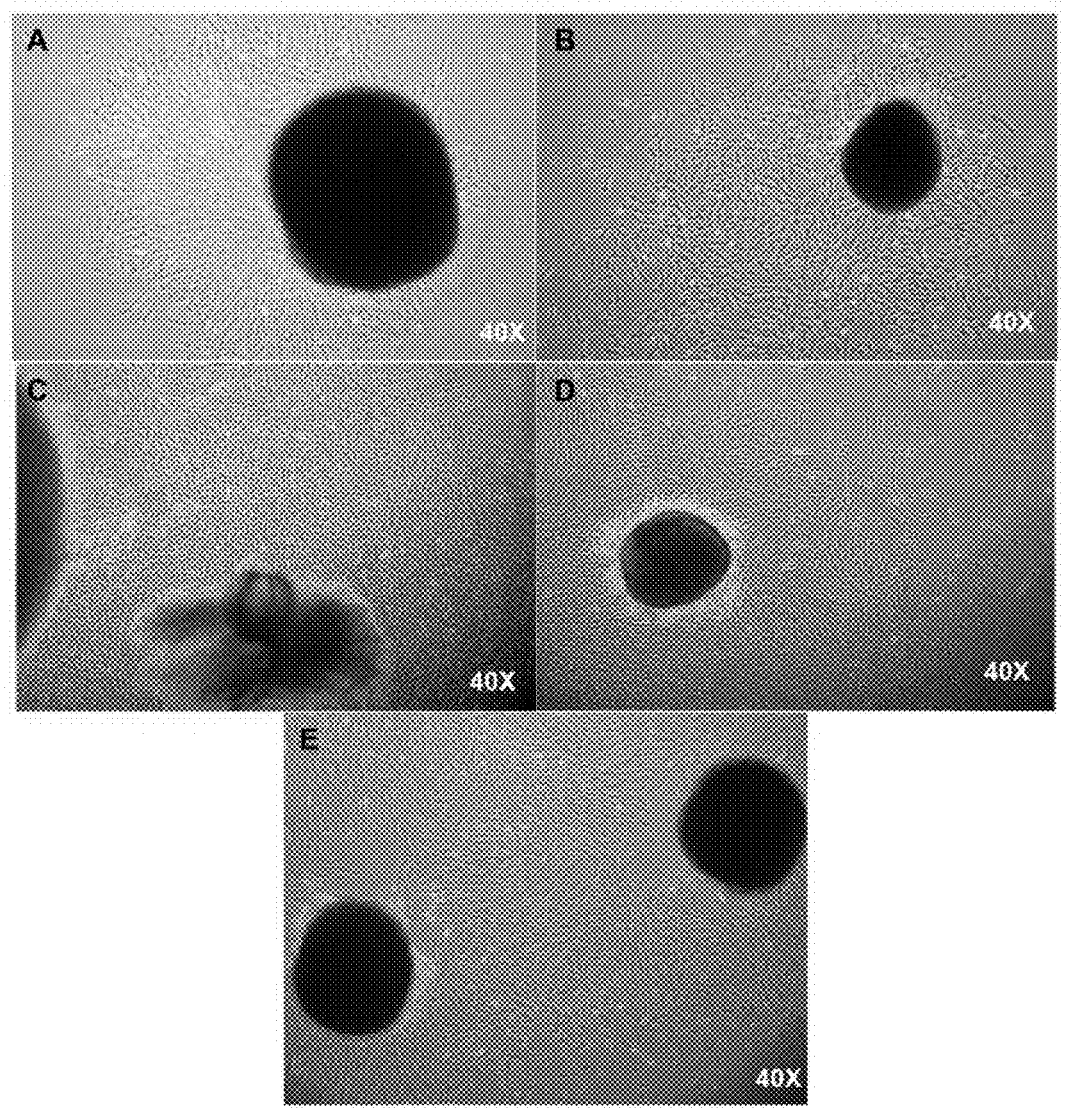
FIGS. 1A-1E are microphotographs showing cells derived from minced cord tissue pieces previously treated with enzyme only without cryopreservation, treated with enzyme before cryopreservation, neither treated with enzyme nor treated with cryopreservation, treated with enzyme after cryopreservation, treated with cryopreservation only without enzyme treatment, respectively.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "an umbilical cord tissue piece", "a minced cord tissue", "cord tissue pieces", "minced cord tissue pieces" are interchangeable. A minced cord tissue piece refers to a piece of cord tissue with a size of less than 0.5 cm. As used herein, the size of a cord tissue piece is no greater than 0.4 cm, or no greater than 0.3 cm, or no greater than 0.2 cm. A cord tissue piece of no greater than 0.2 cm size means the cord tissue piece can pass through 2 mm sieve of a cell strainer.

As used herein, "a segment of an umbilical cord" refers to a portion of an umbilical cord with a length of 0.5 cm or longer than 0.5 cm. A segment of an umbilical cord may be 0.5, 1, 2, or 3 cm, or even long than 3 cm.

"Cryopreservation" or "cryopreserving" is a process where cells or whole tissues are preserved by cooling to low subzero temperatures, such as (typically) 77 K or −196° C. (the boiling point of liquid nitrogen). At these low temperatures, any biological activity, including the biochemical reactions that would lead to cell death, is effectively stopped. However, when cryoprotectant solutions are not used, the cells being preserved are often damaged due to freezing during the approach to low temperatures or warming to room temperature.

The terms "freezing" and "cryopreserving" are interchangeable.

The terms "a cryogenic composition," "a cryogenic solution," "cryopreservation composition," and "anti-freezing solution" are interchangeable.

The terms "cord tissue-derived cells," "cord tissue pieces-derived cells," "cord tissue-derived stem cells," and "cord tissue-derived MSCs" are interchangeable, unless specified otherwise.

The "doubling time" is the period of time required for a quantity to double in size or value.

In one aspect, the invention relates to a method of preserving an umbilical cord. The method comprises: obtaining an umbilical cord; mincing the umbilical cord into cord tissue pieces, wherein each of the cord tissue pieces has a size of no larger than 2 mm; admixing the cord tissue pieces with a cryogenic composition comprising a cryoprotectant and a protein to form a mixture; shaking the mixture for a duration of no shorter than 28 minutes and no longer than 32 minutes; and cryopreserving the mixture.

In another aspect, the invention relates to a method of A method of preserving an umbilical cord, comprising: obtaining an umbilical cord; mincing the umbilical cord into cord tissue pieces; admixing the cord tissue pieces with a cryogenic composition comprising a cryoprotectant and a protein to form a mixture; shaking the mixture for a duration of no shorter than 20 minutes and no longer than 40 minutes; and cryopreserving the mixture.

Further in another aspect, the invention relates to a method of obtaining umbilical cord tissue-derived stem cells from an umbilical cord, comprising: obtaining an umbilical cord; mincing the umbilical cord into cord tissue pieces; admixing the cord tissue pieces with a cryogenic composition comprising a cryoprotectant and a protein to form a mixture; shaking the mixture for a duration of no shorter than 20 minutes and no longer than 40 minutes; and cryopreserving the mixture; thawing the mixture and removing the cryogenic composition; and culturing the cord tissue pieces in a culture media to obtain the umbilical cord-derived stem cells.

In one embodiment of the invention, the culture media comprises human cord blood serum. Alternatively, the culture media consists of DMEM and human cord blood serum.

In another embodiment of the invention, each of the cord tissue pieces has a size of 2 or small than 2 mm (i.e., no larger than 2 mm).

In another embodiment of the invention, the aforementioned method comprises shaking the mixture for a duration of 25-30 minutes.

In another embodiment of the invention, the shaking step is performed for a duration of 28-32 minutes. The shaking step may perform for a duration of 30 minutes.

In another embodiment of the invention, the shaking step is performed at a temperature below 15° C., or a temperature of between 0° C. and 10° C., or at a temperature of no greater than 4° C.

In another embodiment of the invention, the cord tissue pieces are untreated with enzymatic digestion.

In another embodiment of the invention, the cord tissue pieces are treated with enzymatic digestion before the admixing step or after the thawing step. The aforementioned method may further comprise inhibiting the enzymatic digestion with an enzyme inhibitor.

Further in another aspect, the invention relates to a cryogenic composition comprising: a) albumin or human serum; and b) a cryoprotectant, wherein the composition is free of other non-human animal-derived components.

In one embodiment of the invention, the cryoprotectant is at least one chosen from dimethyl sulfoxide (DMSO), glycerol, ethylene glycol and propylene glycol.

In another embodiment of the invention, the cryopreservation solution comprises DMEM or phosphate buffer solution and DMSO or glycerol.

In another embodiment of the invention, the cryopreservation solution comprises DMEM or phosphate buffer solution, and DMSO or glycerol, and human cord blood serum or fetal bovine serum.

In another embodiment of the invention, the cryopreservation solution comprises DMEM or phosphate buffer solution, and DMSO or glycerol, and albumin or plasma protein fraction (PPF).

Alternatively, the cryopreservation solution consists of DMEM, DMSO, dextran and human cord blood serum or albumin.

Further in another embodiment of the invention, the protein component is at least one chosen from albumin, human serum and Plasma protein Fraction (PPF).

Further in another embodiment of the invention, the cryogenic composition is free of non-human animal-derived components and monosaccharide.

Yet in another aspect, the invention relates to a cryogenic composition comprising human cord blood serum 30~50% or albumin 2.5~25%; DMSO 5.5~55%; and dextran 0.5~5%.

In one embodiment of the invention, the cryogenic composition comprises human cord blood serum 40% or albumin 2.5~25%; DMSO 5.5~55%; and dextran 0.5~5%.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods
Cell Culture Media

Commercial media used for culturing cord-derived stem cells included, but not limited to, RPMI, IMDM, DMEM, α-MEM, F12K, McCoy's 5a and X-VIVO 10. In one embodiment of the invention, DMEM (90~70%) and human serum (10~30%) were used for culturing umbilical cord-derived cells.

In some cases, a commercial media was first used to culture cells such as HUVEC, MS-5 or human stroma cell line to obtain a culture media containing factors secreted from the cells. The media that contained cell-secreted factors was collected and used, either with or without a dilution, to replace the commercial media for cell culture.

In some other cases, commercial media contained cell culture additives such as FBS, FCS, human peripheral blood serum, human cord blood serum, platelet rich plasma (PRP), cell growth factors such as IL-3, IL-6, TPO, FltL-3, SCF, EGF, TGF-β, bFGF, Sodium pyruvate, glucose, L-glutamine and/or HEPES.

Alternatively, commercial media containing cell culture additives and cell-secreted factors as aforementioned were used to culture cord-derived stem cells.

Cord Treatment

Umbilical cords were cleaned with alcohol (70~75%) and a phosphate buffer solution. The cords were cut into proper segments and then minced with a mechanical tool into small cord tissue pieces. All tools used were sterilized.

Enzyme Treatment

The effects of enzymatic digestion on the growth of cord tissue-derived cells were evaluated. The cord tissue pieces were not treated with enzyme, or treated with enzyme for 30 minutes before or after cryopreservation. Trypsin or a mixture of trypsin and collagenase was used for enzymatic digestion. Other enzymes that may be used included, but not limited to, dispase, gelatase, hyaluronidase and any combination thereof. The digestion was stopped by an enzyme inhibitor such as human serum (cord blood serum or non-cord blood serum) or fetal calf serum. Other enzyme inhibitors that may be used to replace serum included, but not limited to, trypsin inhibitor, media containing serum (human or non-human animal serum), or a buffer solution containing EDTA. The cells were further washed several times with a buffer solution or a culture media to remove enzyme, then cultured in a culture media for 7 days with changes of the media every 3-7 days.

Cryopreservation

The cord tissue pieces, treated or untreated with enzymatic digestion, were washed with phosphate buffer solution, admixed with a cryopreservation composition, shaked continuously with a rotator (shaker) at a low temperature such as 4° C. for 30 minutes, and then stored for at least one week at a temperature around −196° C. for long term viability using BIOARCHIVE® with robotic liquid nitrogen cryopreservation and storage system. The cryogenic solution contained a buffer solution or a cell culture media and a cryoprotectant. The cryopreservation solution may optionally contain serum from a human source, such as human cord blood serum or human blood serum, and a protein from a human source. The protein may be, but not limited to, albumin or plasma protein fraction (PPF). The buffer solution may be a phosphate buffer solution. The cell culture media may be DMEM. The cryoprotectant may be dimethyl sulfoxide (DMSO), glycerol, ethylene glycol or propylene glycol. The cryopreservation solution may further comprise sucrose, trehalose or dextran.

To assess the effect of cryogenic storage on culture and growth of cord-derived cells from the cord tissue, the above cord tissue pieces were thawed, placed in culture plates with media and cultured in an incubator at 37° C. and 5% $CO_2$.

Cell Count

Cord tissue pieces were cultured in culture media for 7 days, replaced with fresh media and cultured up to 8-14 days. Cells were collected and cell number counted. Cell population doubling time was calculated according to the formula: Doubling time=Culturing hours/$Log_2$ (Cell expanding fold).

Co-Culture of Cord Tissue-Derived Cells with Hematopoietic Stem Cells (HSCs)

The sources of hematopoietic stem cells may come from human umbilical cord blood or peripheral blood. Mononuclear cells were isolated from human umbilical cord blood using FICOLL-PAQUE™ PLUS (GE Healthcare). Purification and isolation of CD34+ hematopoietic stem cells were performed using magnetic activated cell sorting (MACS). Umbilical cord tissue pieces-derived stem cells (MSCs) were seeded onto 6-well plates and cultured for several days in an incubator at 37° C. and 95% moisture. The media was replaced with fresh media containing growth factor. The cord tissue pieces-derived stem cells were then co-cultured with CD34+ hematopoietic stem cells (HSCs) for a week. Every 2-3 days, either the media was replaced or more growth factor was added. The growth factor includes, but not limited to, stem cell factor. (SCF), thrombopoietin (TPO) and Flt3-Ligand (Flt3L). Trypan blue (Invitrogen) and hemocytometer were used for cell count.

RT-PCR technique was used to examine the expression of stem cell early marker genes, and to detect the expression of genes that are involved in cell proliferation-related signal pathways. Total RNA was extracted from cord tissue-derived cells using RNEASY® Mini Kit (Qiagen) according to the manufacture's manual.

Adipogenic Differentiation

The minced cord tissue-derived cells grown in DMEM/serum media to 100% confluency were cultured in serum-free media for 48 hrs and then cultured in adipocyte-inducing media for 4 weeks. The adipocyte-inducing media contained DMEM, serum, antibiotics (streptomycin and penicillin), isobutylmethyl xanthine, dexamethasone, insulin and indomethacin. To identify adipocyte induction, differentiated cells were stained with Oil red O. The positive adipocytes were stained red under a light microscope.

Chondrogenic Differentiation

The minced cord tissue-derived cells grown in DMEM/serum media as aforementioned were collected and cultured in chondrogenic differentiation media for 2 to 3 weeks with replacements of fresh differentiation-inducing media every 3 days. The chondrogenic differentiation media contained DMEM/serum, antibiotics (streptomycin and penicillin), dexamethasone, sodium pyruvate, transforming growth factor-beta 3 (TGF-β 3). Within 14 days of chondrogenic induction, the cells secreted an extracellular matrix incorporating type II collagen, aggrecan, and anionic proteoglycans. The differentiated chondrocyte tissue were frozen, sectioned, and rinsed in acetate solution, and then stained with Alcian blue. The sample sections were counterstained with Nuclear fast red. Differentiation of stem cells into chondrocytes was characterized by appearance of Alcian-stained areas. Strongly acidic sulfated mucosubstance is stained blue; nuclei is stained pink to red; cytoplasm is stained pale pink.

Vasculogenic Differentiation

Cells were seeded on matrigel or collagen-coated plates and cultured in endothelial growth media-2 (EGM-2) for differentiation into vascular endothelial cells.

Duration of Cord Tissue Incubation with Cryogenic Solution

To find an optimal duration for incubation with the cryogenic solution, umbilical cord tissue pieces were admixed with the cryogenic solution and gently shaked with a rotator in a cell culture incubator for various periods of time. Briefly, umbilical cords from 3 donors were collected, a 14 cm-segment taken from each cord. The cord tissues were evenly minced into small pieces (≤2 mm) and divided into 7 equal portions of samples. Each portion of sample was taken at an interval of 10 minutes for 60 minutes to mix with the cryogenic solution in a 15 ml centrifuge tube and shaked with a rotator. At the end of 60 minutes, all the 7 samples were simultaneously cryopreserved according to a standard cryopreservation method. After cryopreservation for 3 days, all the 7 samples were simultaneously thawed, the cryogenic solution removed, and the cord tissue pieces were cultured for 10 days. The numbers of colony forming units and the cord tissue-derived stem cells from each sample were counted.

Results

The cord tissue piece-derived cells were mesenchymal stem cells (MSCs). FIGS. 1A-1D show cord tissue-derived cells on a Day-7 cell culture of a cord tissue piece. The cells had a spindle-like shape and proliferated fast. The cord tissue piece was treated with enzyme digestion only (FIG. 1A), or enzyme digestion and cryopreservation (FIG. 1B), or a fresh cord tissue piece that was untreated with enzyme digestion nor treated with cryopreservation (FIG. 1C), or treated with cryopreservation and then enzyme digestion (FIG. 1D), or treated with cryopreservation only (FIG. 1E) before the cell culture for obtaining cord-tissue derived cells. The results showed that cryopreservation and/or enzyme treatment did not affect the shape of the cells derived from the cord tissue pieces.

Figure 2A:
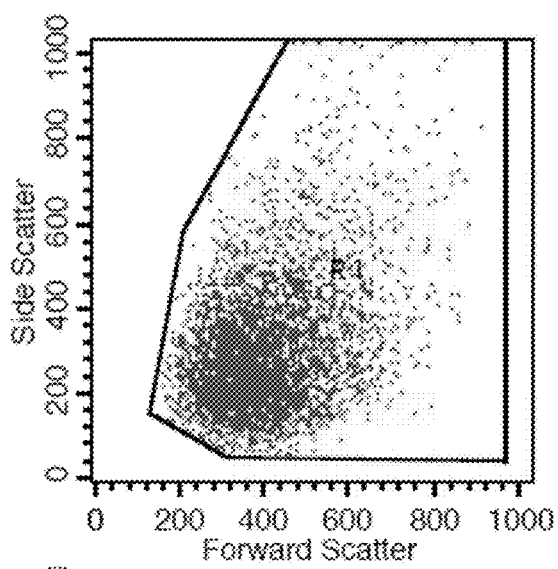
FIGS. 2A-C are plots showing the results of FACS (Fluorescence Activated Cell Sorting or flow cytometry) analysis on the cells derived from minced cord tissue pieces previously treated with enzyme before cryopreservation, treated with enzyme after cryopreservation, and treated with cryopreservation only without enzyme treatment, respectively.
Figure 2B:
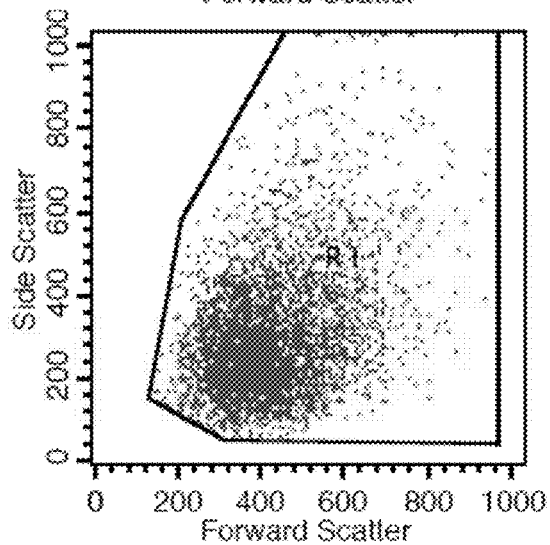
Figure 2C:
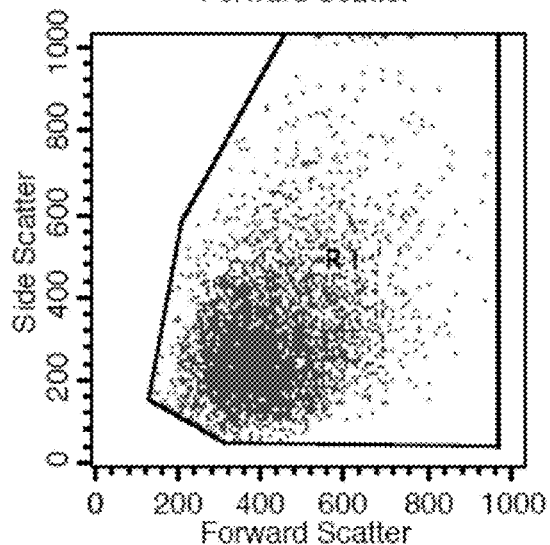

The cell type of the cord tissue-derived cells was evaluated using FACS (Fluorescence Activated Cell Sorting or flow cytometry). To analyze cell surface antigens, cord tissue pieces-derived cells were collected, washed with a phosphate buffer solution, and reacted respectively with antibodies CD13, CD29, CD31, CD34, CD44, CD45, CD73, CD90, CD105, HLA-ABC, HLA-DR, 7AAD or SSEA-4, conjugated with fluorescein isothiocyanate (FITC), phycoerythrin (PE) or Phycoerythrin-Cyanine Dyes 5 (PE-Cy5) (BD Bioscience). FIGS. 2A-2C show scatter dot plots of cells derived from the explants of cord tissue pieces that were treated with enzyme digestion either before (FIG. 2A) or after (FIG. 2B) cryopreservation, or treated with cryopreservation only, i.e., without enzyme treatment (FIG. 2C) prior to the culturing of the explants of the cord tissue pieces. Each dot represents a single cell; its position indicates its forward scatter (FSC) intensity value (cell size), and its side scatter (SSC) intensity value (cell granularity). Forward scatter is roughly proportional to the diameter of the cell. Side scatter is proportional to the granularity. The results indicated that previous treatments of cord tissue pieces with enzyme and cryopreservation, according to the methods of the invention, did not affect the purity and identify of the cells derived from the cord tissue pieces. To analyze cell surface antigens, cord tissue pieces-derived cells were collected, washed with a phosphate buffer solution, and reacted respectively with antibodies CD13, CD29, CD31, CD34, CD44, CD45, CD73, CD90, CD105, HLA-ABC, HLA-DR, 7AAD or SSEA-4, conjugated with fluorescein isothiocyanate (FITC), phycoerythrin (PE) or Phycoerythrin-Cyanine Dyes 5 (PE-Cy5) (BD Bioscience). The results indicated that the types of antigens identified on the surface of the cells derived from the cord tissue pieces treated with enzyme before cryopreservation, or after cryopreservation, or without enzyme treatment either before or after cryopreservation, were all the same (data not shown).

Figure 3:
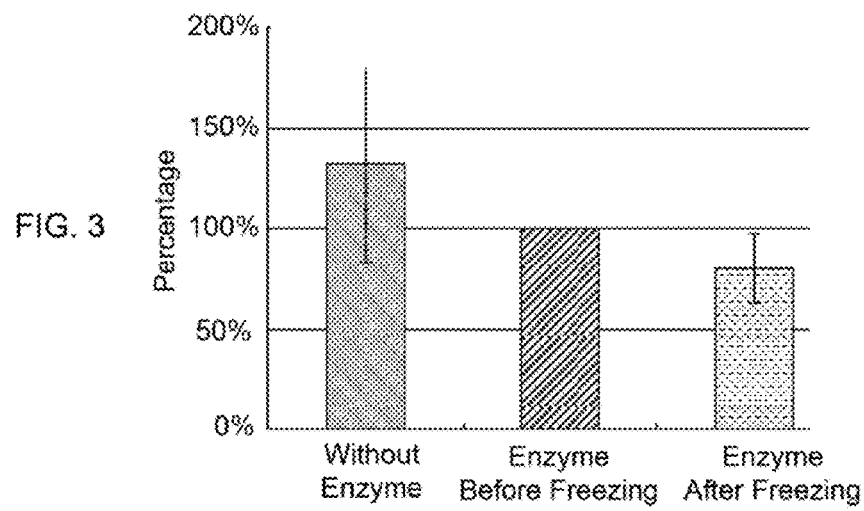
FIG. 3 is a graph showing the number of cells derived from minced cord tissue pieces with or without enzyme treatment before or after cryopreservation.

The effect of enzyme treatment, either before or after cryopreservation of the cord tissue pieces, on the quantity of the cord tissue-derived cells was evaluated. The data were expressed as the relative cell number (%). The number of the cells derived from a thawed cord tissue piece that was treated with enzyme digestion before cryopreservation was considered to be 100% (FIG. 3: Before). The results indicated difference in the cell number as to whether the cord tissue pieces were treated or un-treated with enzyme (FIG. 3: No), or whether the cord tissue pieces were treated with enzyme before or after cryopreservation (FIG. 3: Before; After). Furthermore, replacing serum with trypsin inhibitor as an enzyme inhibitor to stop enzyme digestion did not significantly affect the number of the cells collected (data not shown). In the comparative studies, only 1 piece of the cord tissue was used in each group of the experiment.

Figure 4:
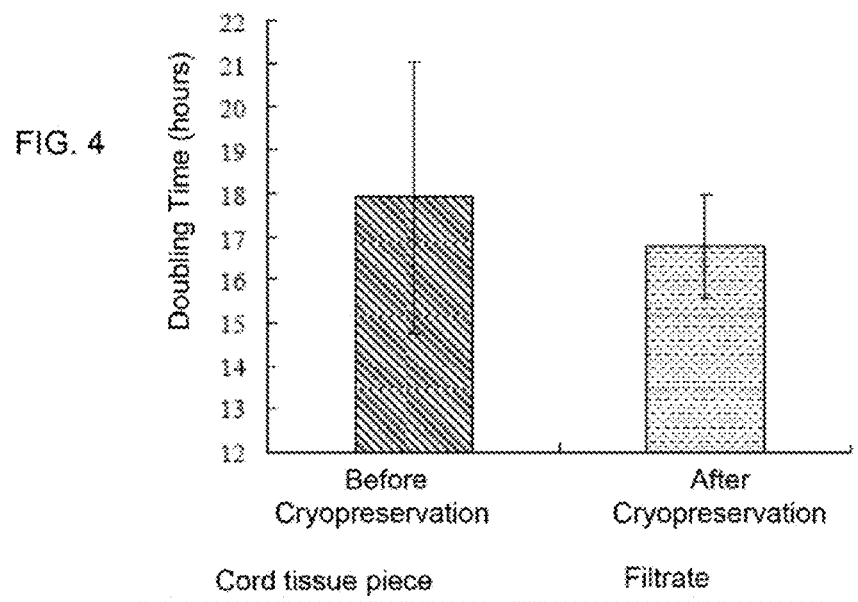
FIG. 4 is a graph showing doubling time of the cells derived from minced cord tissue pieces with or without cryopreservation.

The effect of cryopreservation on the cell population doubling time was examined by comparing the doubling time of the cells derived from a cord tissue piece before cryopreservation (i.e., without cryopreservation treatment) and that of the cells derived from a thawed cord tissue piece after one week of cryopreservation. The results indicated that cryopreservation of cord tissue pieces, according to the invention, does not significantly affect the cell doubling time (FIG. 4). Thus, the yield of the cord tissue piece-derived MSCs was not adversely affected by the freezing and storage process according to the invention.

The effect of replacing serum in the cryopreservation solution with albumin on the yield of the cord tissue piece-derived cells was also investigated. The results showed that there was not a significant difference in the cell number when albumin was used to replace serum in the cryopreservation composition. This finding was meaningful because it provided a workable, serum-free cryogenic composition.

Figure 5:
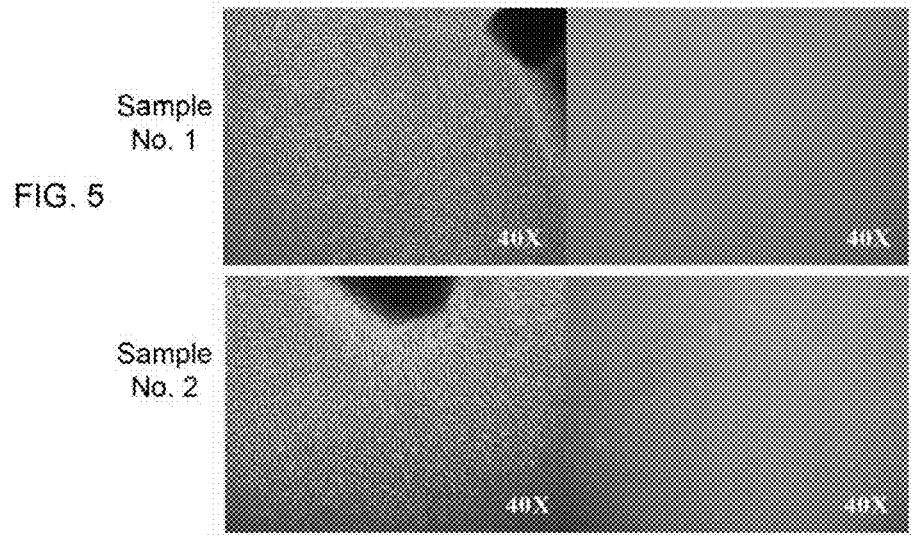
FIG. 5 are microphotographs showing the cell culture of minced cord tissue pieces (left panels) and filtrates (right panels).

The results shown in FIG. 5 demonstrate that cells grown and proliferated in the tissue culture plates were derived from the cord tissue pieces, rather than from free cells in the cord tissue sample. The cord tissue pieces were mixed with a buffer solution and filtered through a cell strainer with 100 μm mesh size (Cell Strainer, BD FALCON™). The cord tissue pieces and the buffer solution (i.e., filtrate or flow through) that passed through the mesh were separately cultured in a culture media for cord tissue-derived cells. The results showed that only the culture plate that contained cord tissue pieces had cells growing and migrating out but not the culture plate that contained the filtrate. In other words, the cells (i.e., mesenchymal stem cells) derived from the cord tissue pieces, according to the invention; did not originate from any wondering, free cells but originated from a stem cell residing within the cord tissue. In other words, those stem cells originated from the cord tissue piece and migrated out from the tissue explant in the culture condition.

To evaluate the effect of mincing on the growth of cord tissue-derived stem cells, a segment of umbilical cord of an appropriate length (about 2 cm) without being minced was directly admixed with the cryopreservation solution and cryopreserved at −160° C. for 5-7 days, then thawed and cultured to grow cord tissue-derived cells. For comparison, another segment of umbilical cord of the same source was minced, admixed with the cryogenic solution and cryopreserved under the same condition, then thawed and cultured. Cell growth was examined under a microscope. The results indicated that cells grew in either group regardless whether the umbilical cord tissue is minced or not.

Figure 6A:
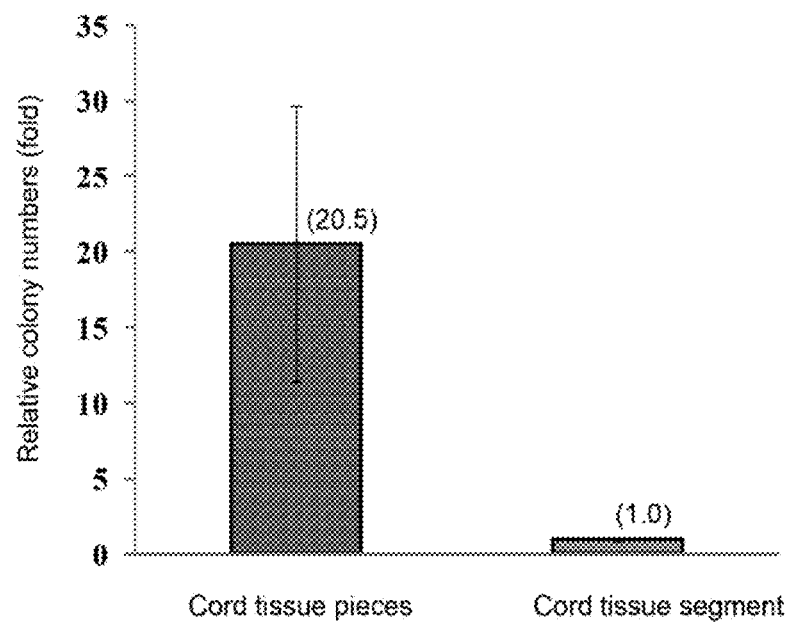
FIGS. 6A-B are graphs showing the numbers of the cells and colonies derived from minced cord tissue pieces and non-minced cord tissue segment, respectively.
Figure 6B:
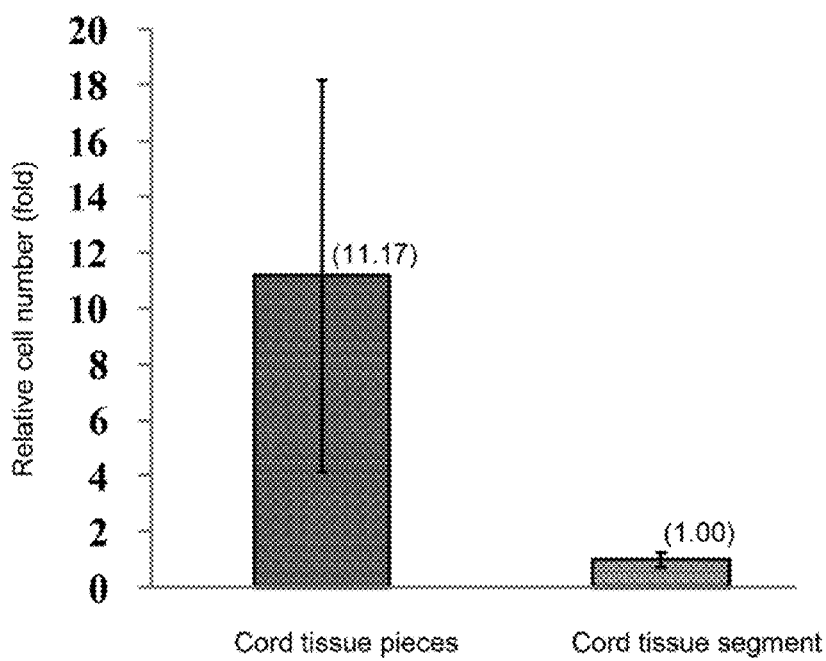

The number of cell colonies on Day-10 cell culture was counted. FIG. 6A shows the cell colony number derived from the minced cord tissue pieces was 20.5-fold of that derived from the non-minced cord tissue segment. The cell colony number was counted based on the number of cord tissue pieces which had stem cells migrating out. In other words, the number of cord pieces that had stem cells migrating out was counted as the number of cell colonies. FIG. 6B shows the relative cell number of the cells derived from the minced cord tissue pieces was 11.17-fold of that derived from the non-minced cord tissue segment. The results indicated that mincing a cord tissue into small pieces affected the yield of the stem cells derived from the cord tissue. Thus, the results indicated cryopreservation of minced cord tissues, according to the invention, gave much higher yield of cord tissue-derived stem cells than cryopreservation of non-minced cord tissues. The finding had important clinical implications because it is crucial to provide sufficient number of stem cells in a short period of time to minimize the risk of cell therapy.

Figure 7:
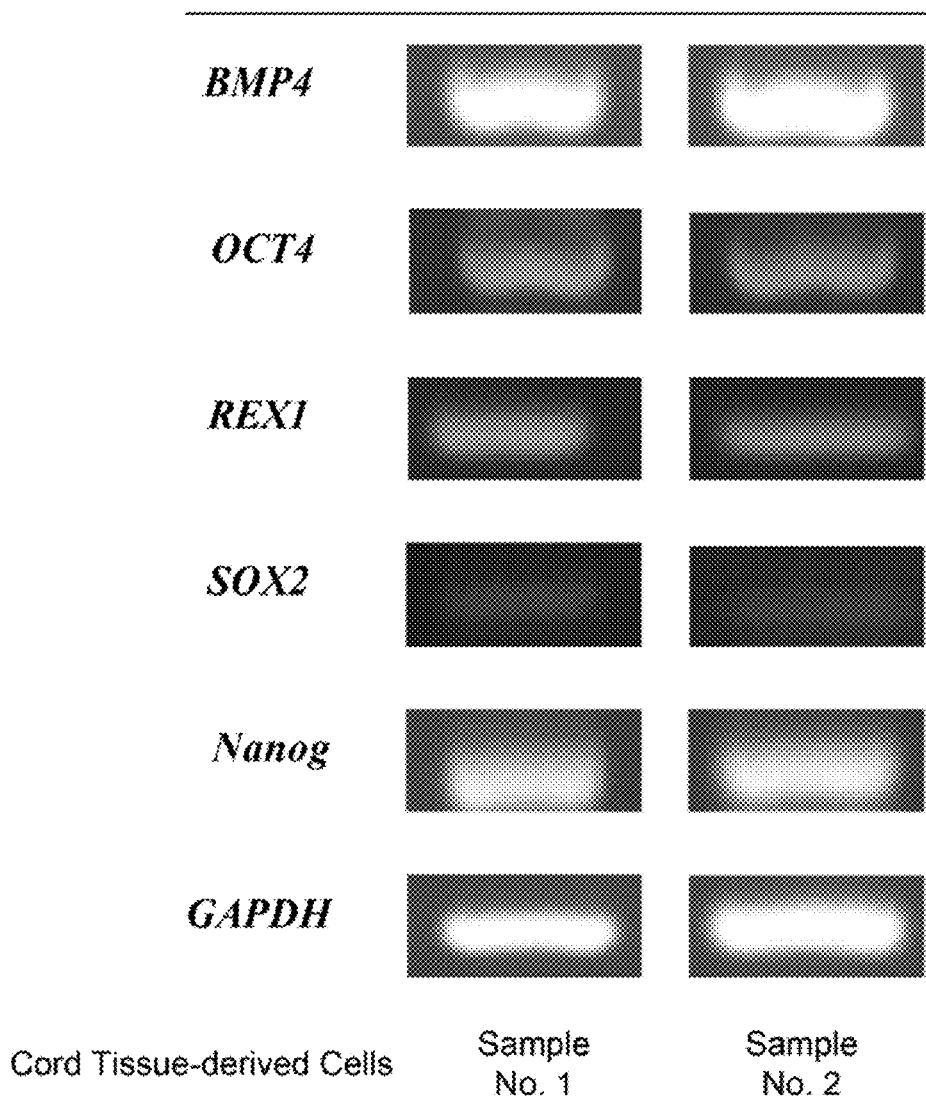
FIG. 7 shows the results of RT-PCR analysis on stem cell marker genes.

These cord tissue-derived cells expressed pluripotent stem cell markers such as BMP4, Oct4, REX1, SOX2 and Nanog. The agarose gel bands shown in FIG. 7 were RT-PCR DNA products, indicating gene expression of those stem cell markers in the cells derived from the minced umbilical cord tissues. The results indicated that stem cells derived from the minced pieces of cord tissue, according to the invention, were pluripotent, early stage stem cells.

Figure 8A:
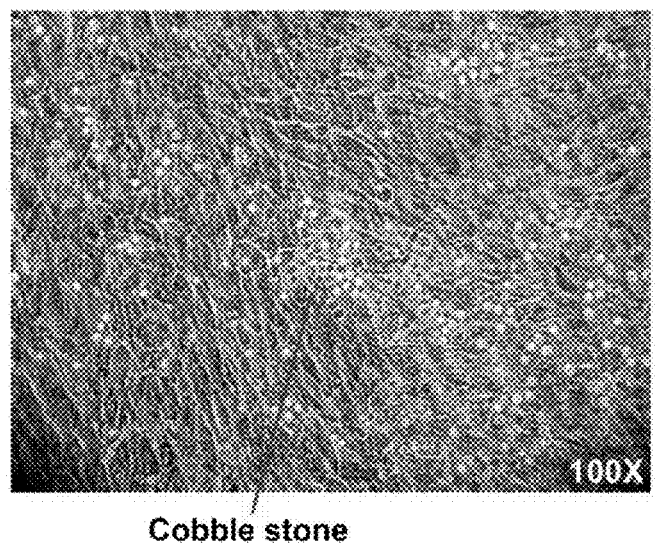
FIG. 8A is a microphotograph showing cobble stone formation in a co-culture of minced cord tissue-derived stem cells and hematopoietic stem cells.

The stem cells derived from the minced cord tissue pieces, according to the invention, could serve as feeder cells for supporting growth and proliferation of hematopoietic stem cells (HSCs). Co-culture of cord tissue-derived cells and HSCs permitted formation of a cobble stone (FIG. 8A). A cobble stone is a cluster of HSCs cells that look dull cobblestone-like under phase contrast microscopy. It is formed because HSCs that are floating loosely on top of the feeder cells are spherical and thus refractile, and HSCs that creep beneath the feeder cells are flattened and, thus, not refractile. The results indicated that growth of HSCs was promoted by co-culturing with cord tissue piece-derived stem cells.

Figure 8B:
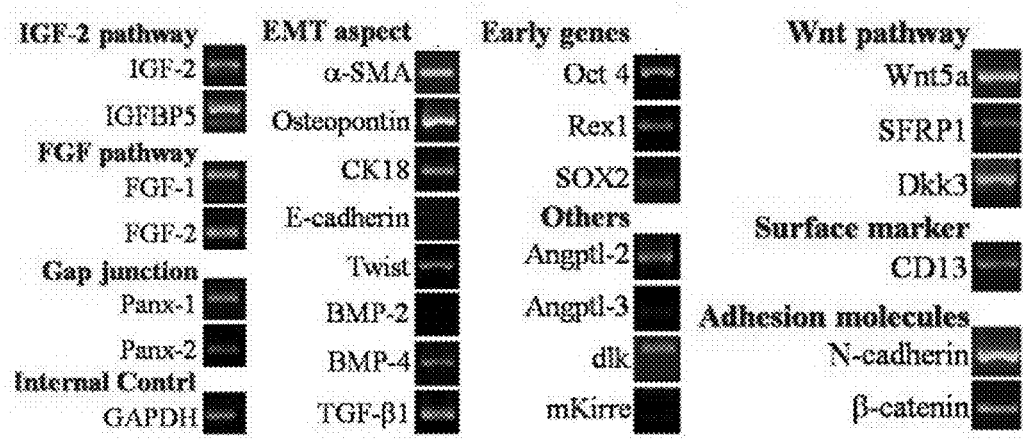
FIG. 8B shows the results of RT-PCR analysis of signaling pathways associated with cell proliferation on cord tissue-derived stem cells.

Signaling pathways that are associated with cell proliferation were detected in the cord tissue-derived stem cells obtained according to the invention. FIG. 8B shows the detected signals included the IGF-2 signaling pathway, such as IGF-2 and IGFBP5, FGF signaling pathway, such as FGF-1 and FGF-2, Gap junction signaling pathway, Panx-1, Panx-2, EMT pathway, such as α-SMA, Osteopontin, CK18, Twist, BMP-4, TGF-β1, Early genes, such as Oct 4, Rex1, SOX2, other genes such as Angiopoietin-like 2 (Angptl-2), dlk, Wnt pathway, such as Wnt5a, SFRP1, Dkk3, Surface Maraker, such as CD13, and adhesion molecules, such as N-cadherin, β-catenin.

Figure 9A:
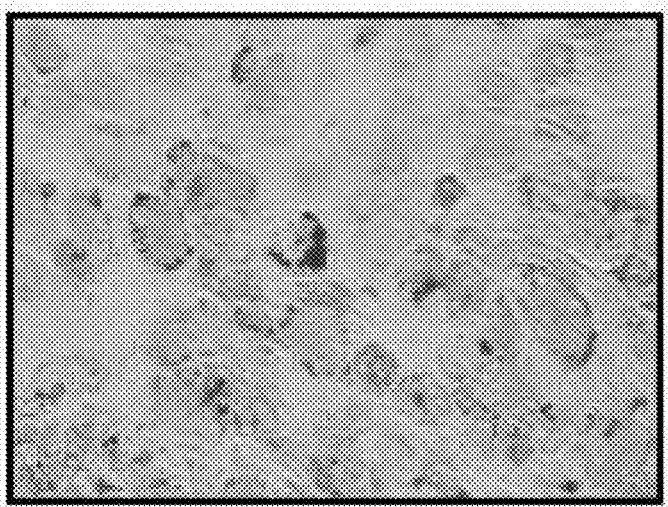
FIGS. 9A-C show microphotographs of adipocytes, chondrocytes and vascular endothelial cells, respectively, differentiated from minced cord tissue-derived stem cells.
Figure 9B:
Figure 9C:
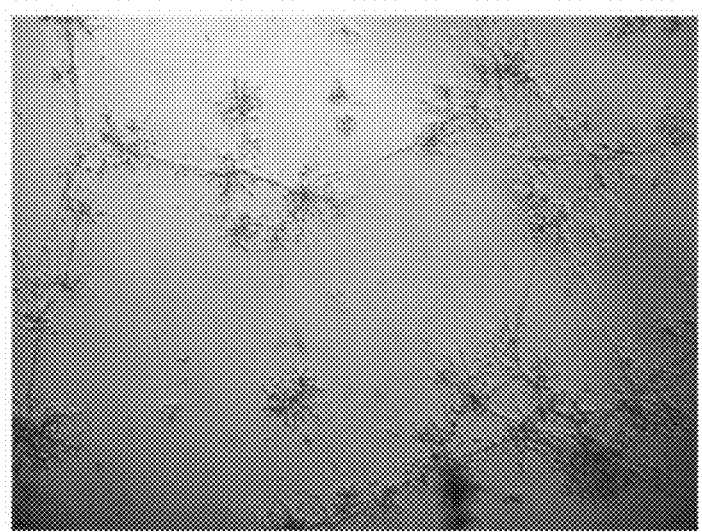

The minced cord tissue-derived cells were pluripotent stem cells capable of adipogenesis, chondrogenesis, vasculogenesis and angiogenesis. FIG. 9A shows Oil-red stained adipocytes differentiated from cord tissue-derived stem cells after 4 weeks of culture in adipogenic media. Culture in chondrogenic media for 2-3 weeks induced cord tissue-derived stem cells to differentiate into chondrocytes, which were stained positively by Alcian blue (FIG. 9B). Enothelial growth media-2 (EGM-2) induced the cord tissue-derived stem cells to differentiate into vascular endothelial cells (FIG. 9C), where the differentiated cells became elongated and interconnected, forming capillary-like networks.

Figure 10:
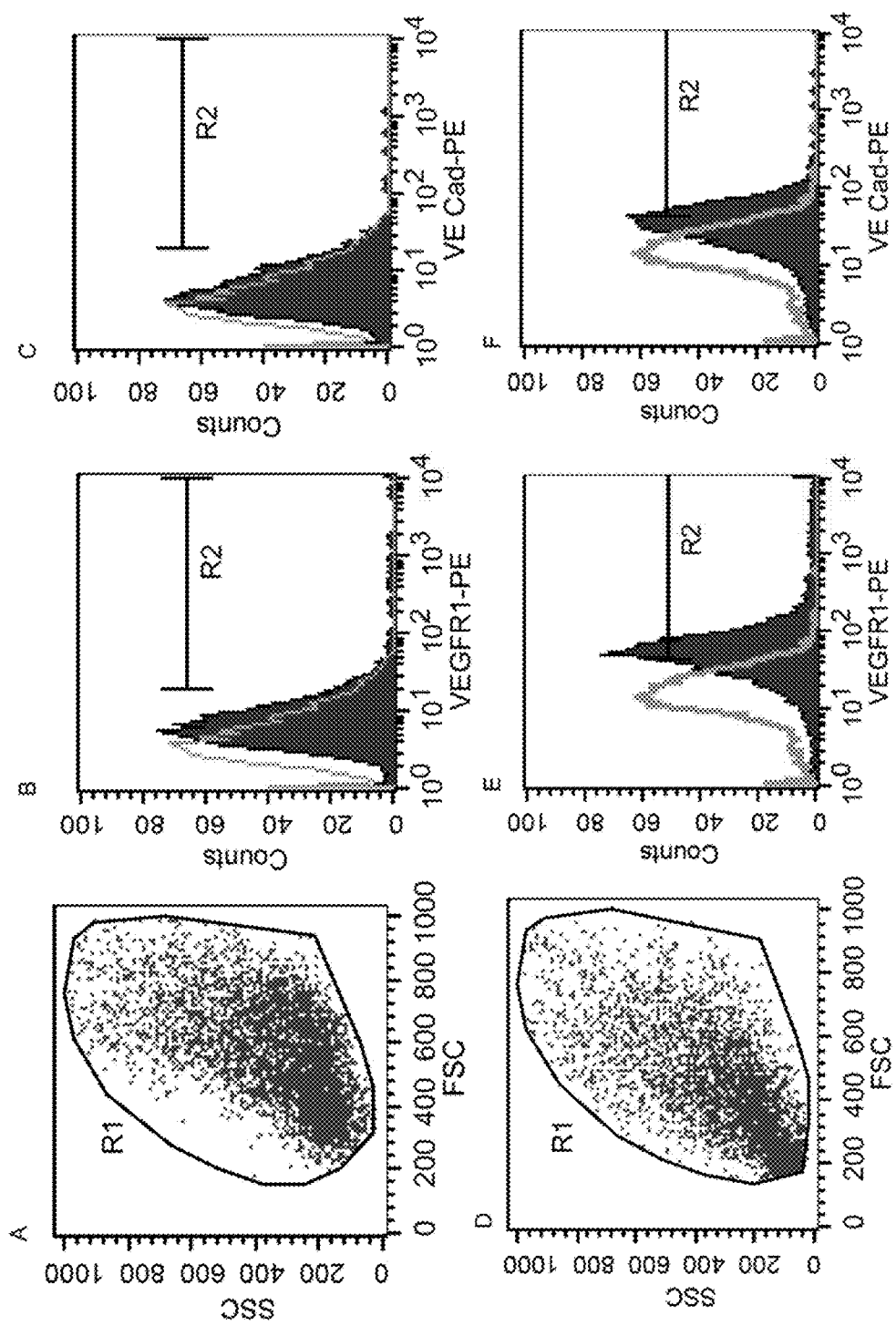
FIGS. 10A-F are plots showing the results of FACS (Fluorescence Activated Cell Sorting or flow cytometry) analysis on the cells before (FIGS. 10A-C) and after (FIG. 10D-F) vasculogenesis induction.

Flow cytometry was used to investigate the changes in the size (diameter), granularity, and surface antigens of the cells before and after induction of vasculogenesis. FIGS. 10A and D show there were changes in both the cell size and granularity. In addition, the differentiation-induced cells showed positive staining with anti-VEGF-R1 and anti-VE-Cad antibodies (FIGS. 10B, C, E and F), which indicated that the differentiated cells possessed characteristics of vascular endothelial cells.

Figure 11:
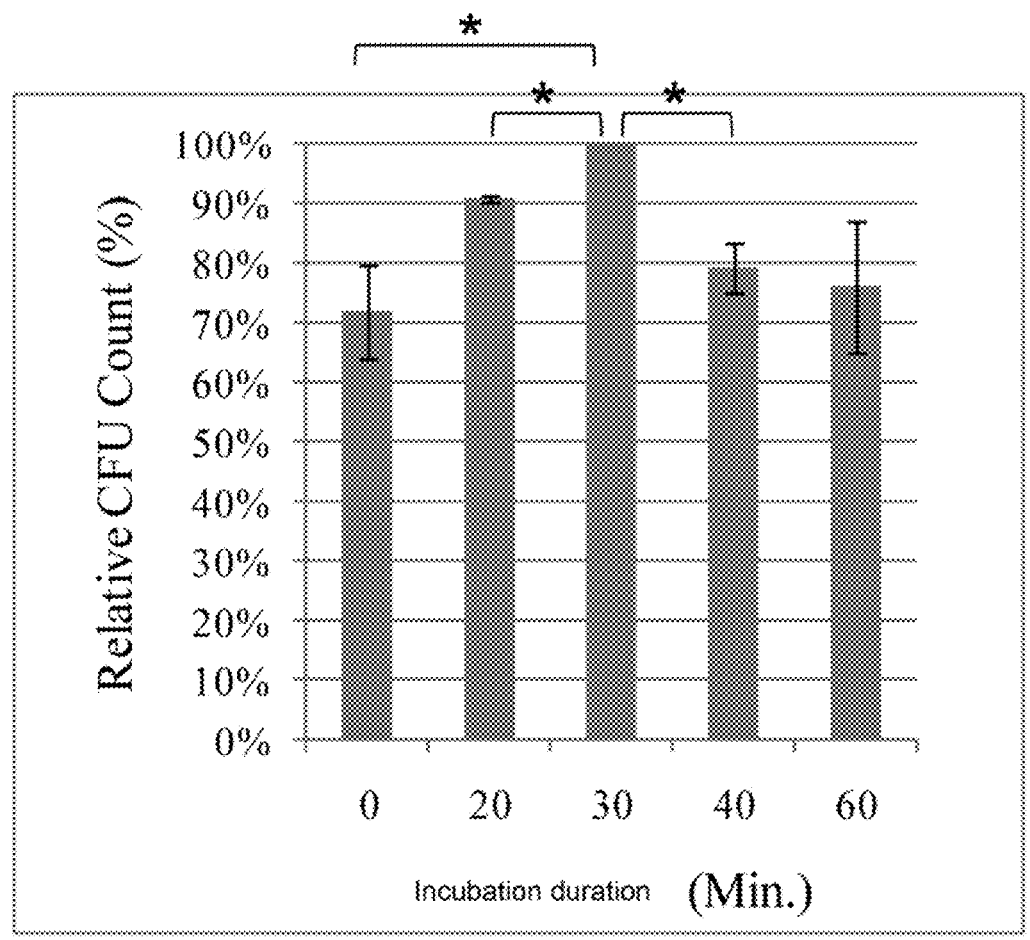
FIG. 11 shows the number of stem cell colony forming units versus the duration of cord tissue incubation with the cryoprotective solution.

The ability of cryopreserved cord tissue pieces to produce cord-derived stem cells was affected by the cord tissue's incubation duration with the cryogenic solution. FIG. 11 shows the number of colony forming units (CFU) versus the cryogenic solution incubation duration. The CFU from each sample exposed to a different incubation duration with the crytogenic solution was compared with that from the sample exposed to 30 minutes' incubation. Experiments were performed with 3 donor samples (n=3). P value≤0.05 is marked with an asterisk. Bar is shown as mean±SEM. The results indicated that the appropriate incubation period with the cryogenic solution was between 20 and 40 minutes. The optimal incubation period was 30 minutes. The cord tissue pieces from the 0-20 minutes of cryogenic solution incubation period did not attach to the culture plate well. The attachment of the cord tissue pieces to the plate made the MSCs easier to adhere and grew on the plate. The cord tissue pieces from the 40-60 minutes of cryogenic solution incubation period did not produce consistent yield of cord tissue-derived MSCs due to a wide variation of cell number count among experimental replicates (data not shown).

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of preserving an umbilical cord tissue, comprising:
   obtaining an umbilical cord;
   mincing the umbilical cord into cord tissue pieces;
   treating the cord tissue pieces with a digestive enzyme solution;
   admixing the cord tissue pieces with a cryogenic composition comprising a cryoprotectant and a protein to form a mixture containing the cord tissue pieces;
   shaking the mixture containing the cord tissue pieces for a duration of no shorter than 20 minutes and no longer than 40 minutes; and
   cryopreserving the mixture containing the cord tissue pieces.

2. The method of claim 1, wherein each of the cord tissue pieces has a size of 2 or smaller than 2 mm.

3. The method of claim 1, comprising shaking the mixture containing the cord tissue pieces for a duration of 25-35 minutes.

4. The method of claim 1, wherein the shaking step is performed at a temperature below 15° C.

5. The method of claim 4, wherein the shaking step is performed at a temperature between 0° C. and 10° C.

6. The method of claim 5, wherein the shaking step is performed at a temperature of no greater than 4° C.

7. The method of claim 1, wherein the shaking step is performed for a duration of 28-32 minutes.

8. The method of claim 1, wherein each of the cord tissue pieces has a size of no larger than 2 mm and the shaking step is performed for a duration of no shorter than 28 minutes and no longer than 32 minutes.

9. The method of claim 1, further comprising adding an enzyme inhibitor to inhibit the digestive enzyme.

10. The method of claim 1, wherein the cryoprotectant is at least one-selected from the group consisting of dimethyl sulfoxide (DMSO), glycerol, ethylene glycol and propylene glycol.

11. The method of claim 1, wherein the protein component is at least one-selected from the group consisting of albumin, human serum and Plasma protein Fraction (PPF).

12. The method of claim 1, wherein the cryogenic composition comprises:
   (a) human umbilical cord blood serum 30~50% or albumin 2.5~25%;
   (b) DMSO 5.5~55%; and
   (c) dextran 0.5~5%.

13. A method of obtaining umbilical cord tissue-derived stem cells, comprising:
   obtaining an umbilical cord;
   mincing the umbilical cord into cord tissue pieces;
   treating the cord tissue pieces with a digestive enzyme solution;
   admixing the cord tissue pieces with a cryogenic composition comprising a cryoprotectant and a protein to form a mixture containing the cord tissue pieces;
   shaking the mixture containing the cord tissue pieces for a duration of no shorter than 20 minutes and no longer than 40 minutes; and
   cryopreserving the mixture containing the cord tissue pieces;
   thawing the mixture containing the cord tissue pieces and removing the cryogenic composition; and
   culturing the cord tissue pieces in a culture media to obtain the umbilical cord tissue- derived stem cells.

14. The method of claim 13, wherein the culture media comprises human serum.

15. The method of claim 13, wherein each of the cord tissue pieces has a size of 2 or smaller than 2 mm.

16. The method of claim 13, comprising shaking the mixture containing the cord tissue pieces for a duration of 25-35 minutes.

* * * * *